United States Patent [19]

Asmus et al.

[11] Patent Number: 4,931,282

[45] Date of Patent: * Jun. 5, 1990

[54] PRESSURE-SENSITIVE MEDICAL SEALANT

[75] Inventors: Robert A. Asmus, Hudson, Wis.; Daniel C. Duan, St. Paul, Minn.

[73] Assignee: Minnesota Mining and Manufacturing Company, Minn.

[*] Notice: The portion of the term of this patent subsequent to Jul. 18, 2006 has been disclaimed.

[21] Appl. No.: 125,377

[22] Filed: Nov. 25, 1987

[51] Int. Cl.$^5$ .................. A61K 9/14; A61K 31/79; A61L 15/06; A61L 25/00

[52] U.S. Cl. ..................... 424/448; 424/78; 424/80; 424/443; 514/210

[58] Field of Search ............. 424/78, 80, 220, 429, 424/443, 448; 428/220; 514/210, 227, 953

[56] References Cited

U.S. PATENT DOCUMENTS

| | | | |
|---|---|---|---|
| 3,220,960 | 11/1965 | Wichterle et al. | 260/2.5 |
| 3,252,995 | 5/1966 | Grosser et al. | 260/326.5 |
| 3,294,765 | 12/1966 | Hort et al. | 260/80.3 |
| 3,551,556 | 12/1970 | Kliment et al. | 424/21 |
| 3,689,439 | 9/1972 | Field et al. | 260/2.5 N |
| 3,907,720 | 9/1975 | Field et al. | 260/2.5 R |
| 3,928,255 | 12/1975 | Milkovich et al. | 260/2.5 R |
| 4,058,491 | 11/1977 | Steckler | 260/2.2 R |
| 4,300,820 | 11/1981 | Shah | 525/206 |
| 4,310,509 | 1/1982 | Berglund et al. | 424/28 |
| 4,323,557 | 4/1982 | Rosso et al. | 424/28 |
| 4,364,929 | 12/1982 | Sasmor et al. | 424/80 |
| 4,367,297 | 1/1983 | Hubner et al. | 523/130 |
| 4,436,887 | 3/1984 | Chromecek et al. | 526/263 |
| 4,543,371 | 9/1985 | Gallop et al. | 523/106 |
| 4,554,924 | 11/1985 | Engel | 128/640 |
| 4,584,192 | 4/1986 | Dell et al. | 514/635 |
| 4,621,029 | 11/1986 | Kawaguchi | 428/447 |
| 4,676,782 | 6/1987 | Yamamoto et al. | 604/175 |

FOREIGN PATENT DOCUMENTS

| | | |
|---|---|---|
| 0107376 | 6/1983 | European Pat. Off. |
| 1511563 | 6/1975 | United Kingdom. |
| 2115431 | 2/1983 | United Kingdom. |

OTHER PUBLICATIONS

U.S. Ser. No. 902,396, "Electrically-Conductive, Pressure-Sensitive Adhesive and Biomedical Electrodes" filed Sep. 5, 1986 in the name of Michael R. Engel and assigned to Minnesota Mining and Manufacturing Company.

"Risk of Infection with Intravenous Indwelling Catheters: Effect of Application of Antibiotic Ointment" by Zinner et al, in The Journal of Infectious Diseases, vol. 120, No. 5, Nov. 1969.

"Application of Antibiotic Ointment to the Site or Venous Catheterization-A Controlled Trial" by Norden, in The Journal of Infectious Diseases, vol. 120, No. 5, Nov. 1969.

"A Comparative Study of Polyantibiotic and Iodophor Ointments in Prevention of Vascular Catheter-Related Infection" by Maki and Band, in The American Journal of Medicine, vol. 70, Mar. 1981.

"Surgical Skin Prep Regimens: Comparison of Antimicrobial Efficacy" by Ulrich, in Infections in Surgery, Aug. 1984.

"Updated In Vivo Methods for Evaluating Topical Antimicrobial Agents on Human Skin" by Leyden et al, in The Journal of Investigative Dermatology, vol. 72, No. 4.

*Primary Examiner*—John Kight, III
*Assistant Examiner*—C. Azpuru

[57] ABSTRACT

A pressure-sensitive medical sealant composition comprising (a) a crosslinked, swellable polymeric matrix made from an N-vinyl lactam monomer and a multiethylenically unsaturated compound, wherein the ethylenic groups are vinyl groups, allyl groups or methallyl groups, which groups are bonded to nitrogen or oxygen atoms; (b) a plasticizer; and (c) an antimicrobial. The medical sealant is highly moisture vapor transmissive and is capable of incorporating large concentrations of iodine. The composition can be used in a variety of medical applications including as a teat plug, a wound or burn dressing, or as a sealant to seal junctions between medical instruments penetrating the skin and the skin. A method of preparing the medical sealant composition in a caulkable form is also disclosed.

18 Claims, No Drawings

PRESSURE-SENSITIVE MEDICAL SEALANT

FIELD OF THE INVENTION

This invention relates to a medical sealant composition principally for sealing a junction between living skin and a medical instrument penetrating through the skin. Specifically, this invention relates to a medical sealant composition comprising a crosslinked polymer, prepared from an N-vinyl lactam monomer and an antimicrobial incorporated into a plasticizing solution. In its preferred embodiment, the invention relates to a medical sealant comprised of N-vinyl-2-pyrrolidone crosslinked with 3,3'-ethylidene bis(N-vinyl-2-pYrrolidone) and iodine swelled with a solution of glycerol in water. These medical sealants are pressure-sensitive adhesive, highly moisture vapor transmissive and capable of complexing with iodine. In use these medical sealants have surprisingly high antimicrobial activity, yet are nonirritating to the skin. This invention further relates to a method of preparing a caulkable medical sealant by grinding the crosslinked polymer into a powder before swelling it with the plasticizing solution.

BACKGROUND OF THE INVENTION

Catheter related septicemia is a serious problem potentially affecting an estimated 160 million catheter starts yearly in the U.S. alone. Evidence to date suggests that organisms invade at the catheter site to initiate a local infection. Topical antimicrobials including "Neosporin ® Ointment" commercially available from Burroughs Welcome Co., Research Triangle Park, N.C., and iodophor ointments are widely used in an attempt to provide some protection from microbial invasion. Clinical studies attempting to determine the efficacy of these topical ointments has shown them to be of modest or no benefit in reducing rates of infection (Zinner, S. H., B. C. Denny-Brown, P. Braun, J. P. Burke, P. Toala and E. H. Kass. 1969. "Risk of Infection with Intravenous Indwelling Catheters: Effect of Application of Antibiotic Ointment." *The Journal of Infectious Diseases.* 120: 616–619; Morden, Carl W. 1969. "Application of Antibiotic Ointment to the Site of Venous Catheterization-A Controlled Trial". *The Journal of Infectious Diseases.* 120: 611–615; Maki, Dennis G. and Jeffrey D. Band. 1981. "A Comparative Study of Polyantibiotic and Iodophor Ointments in Prevention of Vascular Catheter-Related Infection". *The American Journal of Medicine.* 70: 739–744). Suggested reasons for the marginal benefits of these ointments have been proposed in the literature. The leading suspect is that since these ointments are petroleum jelly based, they are occlusive and not moisture vapor transmissive. Moisture from the body builds up under the ointment creating a beneficial environment for the bacteria and a pathway to the catheter. Additionally, ointments are greasy and poorly compatible with the transparent dressings or gauze and tape normally used to dress catheters. The ointment will either become absorbed by the gauze or dressing material, thereby not remaining at the site, or the ointments will undermine the adhesion of the transparent dressing and migrate under the dressing, again not remaining in place. This migration of the ointment creates lifting of the dressing and exposes the site to additional contamination. In addition, the antibiotic based ointments are ineffective on resistant bacteria and fungi. In fact in a study by S. H. Zinner et al (supra), 30% of the organisms isolated from catheter tips were resistant to the antibiotic ointment.

Other known medical sealants include one disclosed in U.S. Pat. No. 4,621,029 and comprised of a polysiloxane gel. The sealant is water-repellant and, thus, poorly moisture vapor transmissive. Accordingly moisture from the body can collect under this sealant, creating a beneficial environment for bacteria. Furthermore, polysiloxane gels are not capable of complexing with iodine, a substance which exhibits broad-spectrum antimicrobial activity when placed in contact with mammalian skin.

U.S. Pat. No. 4,364,929 discloses a lubricating gel comprising a physiologically compatible colloidal gel-forming polymer, water and an iodophor or a substance capable of forming an iodophor with iodine. These gels are described as lubricants, indicating that they would not have adhesive properties and would be greasy, and therefore incompatible with conventional wound dressings.

G. B. Pat. Specification No. 1,511,563 discloses a crosslinked hydrophilic polymer comprised of 30 to 90 percent by weight water soluble mono-olefinic monomers, with or without 1 to 70 percent by weight water-insoluble monomers, and 10 to 70 percent by weight of a terminally diolefinic hydrophobic macromer. An especially preferred water-soluble monomer is N-vinyl pyrrolidone. These polymers are particularly useful in medical applications such as bandages for wound treatment and body implants, where strength of the polymer article and high permeability of water are required simultaneously. However, these polymers are not adhesive and therefore would not be useful as medical sealants.

Another pressure-sensitive adhesive for medical applications is disclosed in U.K. Pat. application 2,115,431. The adhesive described comprises at least one irradiation crosslinked synthetic organic polymer and an adhesive plasticizer. The crosslinked polymer is formed by subjecting a solution or dispersion of at least one uncrosslinked, synthetic organic polymer (including one which has repeating units derived from an N-vinyl lactam monomer) in a solubilizing plasticizer to ionization radiation energies of at least the equivalent of 100,000 electron volts (x-ray, gamma ray and electron beam irradiation). Those skilled in the art will appreciate that while the use of ionizing irradiation to force chemical reactions can be useful for many applications, the use of ionizing irradiation is not always desirable because of the wide variety of reactive species that can be produced making the process very difficult to control and making the effect of additional constituents very difficult to predict.

Another art involving polymeric matrices that are swelled in water is the hydrogel art. These compositions are covalently crosslinked and are used extensively in contact lenses. Many of these hydrogels are based on polyvinylpyrrolidone and have been extensively used in medical applications. Because of the long experience with use of polyvinylpyrrolidone in medical applications its safety is well known making it a desirable candidate for biocompatible adhesives. While most hydrogels are not adhesive, EPO Appln. No. 83305770.6 (publication 0107376, 02/05/84) describes a hydrogel which has some tack and is recommended for use as a wound dressing. The hydrogel is prepared by dissolving between 15% and 25% by weight polyvinylpyrrolidone in water and crosslinking with ionizing irradiation (1 to 5 Mrads, electron beam). Here again the ionizing radiation process is not desirable.

U.S. Pat. No. 4,543,371 discloses a hydrogel formed by the copolymerization of a hydrophilic dihydroxy alkyl acrylate or methacrylate, a substantially water insoluble alkyl acrylate or methacrylate, one or more additional hydrophilic monomers selected from the group of vinylic monomers, acrylates, and methacrylates, and a crosslinking agent. The resultant hydrogel is nontacky and is preferably used for the formation of contact lenses having greater rigidity than the hydrogel contact lenses of the prior art.

U.S. Pat. No. 3,928,255 discloses chemically joined, phase separated self-cured hydrophilic thermoplastic graft copolymers which are useful in the field of biomedics. These copolymers comprise at least one hydrophilic ethylenically unsaturated monomer or mixtures thereof and at least one copolymerizable hydrophobic macromolecular monomer having a copolymerizable end group which is copolymerizable with said hydrophilic monomer. The resultant hydrogels are nontacky and are preferably used as contact lenses or artificial organs.

U.S. Pat. No. 3,294,765 discloses polymeric matrices of N-vinyl lactams crosslinked with 3,3'-ethylidene bis(N-vinyl-2-pyrrolidone). The patent indicates that polymeric matrices with mechanical properties ranging from thickened solutions to intractable gels are obtained depending on the relative amount of crosslinker used. None are reported to be adhesive.

U.S. Pat. No. 3,907,720 discloses that iodine complexes can be prepared of water swellable crosslinked N-vinyl lactam or N-alkyl-N-vinylamide polymers in the form of porous beads or granules. These complexes are suitable as bactericide and water treatment aids in gravity filtration systems or packed columns, such aids having the advantage of rapid throughput.

The polymeric compositions known in the art have not met the need for a pressure-sensitive medical sealant that has high moisture vapor transmission and is capable of complexing with and releasing iodine. A need also exists for a medical sealant that is in a caulkable form and can be used to surround and seal a catheter site.

SUMMARY OF THE INVENTION

The present invention provides a medical sealant composition comprising:

(a) a crosslinked, swellable polymeric matrix formed by a free-radical polymerization of at least one polymerizable monomeric species wherein at least about fifty percent of the monomeric component is an N-vinyl lactam, a crosslinker which is a multi-ethylenically unsaturated compound with the ethylenic groups being vinyl, allyl, or methallyl groups bonded to nitrogen or oxygen atoms;

(b) a plasticizing solution; and (c) an antimicrobial which composition is formulated so as to have a T-Peel value of at least about 3 g/cm when measured on low density polyethylene.

The medical sealant of this invention can be formulated so as to have excellent pressure-sensitive adhesive characteristics while tolerating the incorporation of substantial amounts of water and other polar liquids and ionic species. The medical sealant compositions of this invention have surprisingly high moisture vapor transmission rates, and have the ability to incorporate high concentrations of iodine.

The present invention further provides a method of providing the above-described medical sealant composition in an easily deformable, caulkable state.

DETAILED DESCRIPTION OF THE INVENTION

The pressure-sensitive adhesive compositions of the present invention are obtained by the free-radical polymerization, either in bulk or in solution, of a precursor containing an N-vinyl lactam monomer and a crosslinking compound. As examples of N-vinyl lactams which may be employed, the following are illustrative:
N-vinyl-2-pyrrolidone,
5-methyl-N-vinyl-2-pyrrolidone,
5-ethyl-N-vinyl-2-pyrrolidone,
3,3-dimethyl-N-vinyl-2-pyrrolidone,
3-methyl-N-vinyl-2-pyrrolidone,
3-ethyl-N-vinyl-2-pyrrolidone,
4-methyl-N-vinyl-2-pyrrolidone,
4-ethyl-N-vinyl-2-pyrrolidone,
N-vinyl-2-valerolactam, and
N-vinyl-2-caprolactam The amount of N-vinyl lactam monomer in the precursor is generally from about 5 to 99.9 percent by weight of the precursor and preferably about 25 to 99.9 percent by weight of the precursor. The N-vinyl lactam monomer(s) comprises about 50 to 100 percent by weight of the non-crosslinking monomers present in the precursor, and preferably about 90 to 100 percent by weight of the non-crosslinking monomers present in the precursor. Particularly when the precursor is polymerized in bulk, the monomer is preferably 100 percent by weight N-vinyl-2-pyrrolidone.

Other monomers which are soluble in the precursor comprise the remainder of the monomers which may be present. Especially useful monomers are hydroxyalkyl acrylates and methacrylates, such as 2-hydroxyethyl acrylate, 2-hydroxyethyl methacrylate, 2-hydroxypropyl acrylate, 2-hydroxypropyl methacrylate, 2,3-dihydroxypropyl methacrylate, acrylic acid, methacrylic acid and a tertiary amino-methacrylimide, e.g. trimethylamino-methacrylimide. Other useful monomers include water soluble amides, such as N-(hydroxymethyl)acrylamide and -methacrylamide, N-(3-hydroxypropyl)acrylamide, N-(2-hydroxyethyl) methacrylamide, N-(1,1-dimethyl-3-oxabutyl)acrylamide and N-[1,1-dimethyl-2-(hydroxymethyl)-3-oxabutyl]acrylamide; water-soluble hydrazine derivatives, such as trialkylamine methacrylimide, e.g., trimethylamine-methacrylimide and dimethyl-(2-hydroxypropyl)amine methacrylimide; mono-olefinic sulfonic acids and their salts, such as sodium ethylene sulfonate, sodium styrene sulfonate and 2-acrylamido-2-methylpropanesulfonic acid; N-[2-(dimethylamino)ethyl]acrylamide and -methacrylamide, N-[3-(dimethylamino)-2-hydroxypropyl]methacrylamide, N-vinyl-pyrrole, N-vinyl-succinimide, 1-vinyl-imidazole, 1-vinyl-indole, 2-vinyl imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, and 4-acrylyl-morpholine.

The most preferred performance properties for a catheter sealant are provided by requiring that about 100 percent by weight of the monomers are an N-vinyl lactam.

The precursor is further comprised of a crosslinker which is a multi-ethylenically unsaturated compound wherein the ethylenic groups are vinyl groups (including substituted vinyl groups, such as isopropenyl groups), allyl groups, and/or methallyl groups; which groups are bonded to nitrogen or oxygen atoms. Vinyl, allyl and methallyl groups as used herein include substituted versions thereof. Although the exact level of optimum performance will vary depending upon the specific compound used, a relatively low level of crosslinking compound has been found suitable to obtain compositions which are very tacky.

Exemplary crosslinking compounds include divinyl, diallyl or dimethallyl esters (e.g. divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate), divinyl, diallyl or dimethallyl ethers (e.g., diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether), divinyl, diallyl and dimethallyl amides, including bis(N-vinyl lactams), (e.g., 3,3'-ethylidene bis(N-vinyl-2-pyrrolidone), and divinyl, diallyl and dimethallyl ureas. Preferred crosslinking compounds are divinyl adipate, 3,3'-ethylidene bis(N-vinyl-2-pyrrolidone) and diethyleneglycol divinyl ether. When the composition of the present invention is to be used as a catheter sealant, 3,3'-ethylidene bis(N-vinyl-2-pyrrolidone) is the particularly preferred crosslinking compound.

The bis(N-vinyl-lactams) can be used at lower levels than some of the other crosslinkers. Polyfunctional crosslinking agents such as tri- and tetra-functional compounds can also be used, e.g., trivinyl glyceryl ether. Such agents would be used at slightly lower levels than the difunctional crosslinking agents. However, multi-functional acrylate compounds have been found unsuitable as crosslinking compounds when the N-vinyl lactam comprises the majority of the monomeric species used in the composition of this invention.

The level of crosslinking compound in the compositions of the invention will generally be between about 0.02 and about 5.0 percent by weight of the N-vinyl lactam monomer in the composition. These levels generally provide an amount of crosslinking suitable for providing a medical sealant with pressure-sensitive adhesive characteristics. However, different classes of the crosslinking compounds are preferably used at different levels. The divinyl amides, including bis(N-vinyl lactams), and divinyl ureas are preferably used at levels of from about 0.02 percent to about 0.5 percent by weight of the monomer. The divinyl, diallyl, or dimethallyl esters; the diallyl or dimethallyl ethers; the diallyl or dimethallyl amides; and the diallyl or dimethallyl ureas are preferably used at levels of from about 0.05 to about 2 percent by weight of the monomer. The divinyl ethers are preferably used at levels of from about 0.5 to about 5 percent by weight of the monomer.

The compositions of the invention can be optimized by varying parameters such as the amount of light used to initiate polymerization, the amount of initiator, the temperature, the ratios of reactants, the identity of the monomer, the choice of solvent and the amount, if any, present in the reaction mixture, and the like.

The crosslinked polymeric matrix in the compositions of this invention have been found to be stable over long storage periods. The compositions also have high moisture vapor transmission rates, are very hydrophilic and readily absorb and hold water and water-soluble materials.

The compositions of this invention contain a plasticizer for the crosslinked polymer. This plasticizer must not be dermally irritating and must, in admixture with any cosolvents present, act to swell the polymer matrix. Preferred plasticizers are glycerol and mixtures of glycerol and water. Glycerol is the preferred plasticizer because it provides compositions having good adhesion to skin, it functions as a humectant to prevent excessive evaporation of moisture from the final composition, and it is less irritating than other polyol plasticizers such as ethylene glycol, propylene glycol and the like. However, these other polyols as well as water, alcohols (e.g., methanol, ethanol and isopropanol) ether-alcohols (e.g., glycol ethers and polyethylene glycol), amines (e.g. triethanolamine), ester alcohols (e.g. methyl lactate, 2-hydroxyethyl acetate), amides or lactams (e.g., N-methyl pyrrolidone) may be used alone or in admixture with each other. Plasticizers other than glycerol can only be used if they are non-irritating to the skin in the amounts used. The plasticizer is added in an amount sufficient to render the crosslinked polymer or copolymer pressure-sensitive adhesive. In general, the amount of plasticizer will range from about, 55 to about 95 weight percent of the composition. Glycerol is used in an amount up to 100% of the plasticizer, and is preferably 10 to 80 percent by weight of the plasticizer. When water is used in admixture with glycerol, it is usually present in a concentration of at least 20 percent by weight of the plasticizing solution, and preferably about 20 to 90 percent by weight of the plasticizing solution.

The compositions of the present invention further include an antimicrobial. The antimicrobial can be incorporated as a dispersed solid or in solution into the polymer precursor prior to polymerization, provided that the antimicrobial does not interfere with the polymerization process. For example, the antimicrobials parachlorometaxylenol and chlorhexidine gluconate do not interfere with the polymerization process. Alternatively and preferably, a more comprehensive method of incorporating the antimicrobial in the polymeric matrix is to dissolve the antimicrobial in the plasticizer or use a surfactant to create an emulsification of antimicrobial in plasticizer, and swell the polymer matrix with the plasticizer/antimicrobial solution or emulsification. Exemplary antimicrobials include iodine, chlorhexidene gluconate, parachlorometaxylenol, bacitracin salts (e.g., zinc bacitracin), neomycin sulfate, silver sulfadiazine, and polymyxin B sulfate.

Preferably the antimicrobial is present in a concentration of about 0.01 to 10 percent by weight of the total medical sealant composition. More preferably the antimicrobial is present in a concentration of between about 0.5 and 2.0 percent by weight of the total composition.

Additives can be incorporated in the medical sealant compositions of this invention to improve the sealants' physical or antimicrobial properties. For example, where iodine is used as the antimicrobial, the addition of sodium iodide enhances the solubility of the iodine and reduces the free iodine concentration. Buffering the pH of the sealant composition is useful for providing a non-irritating composition for sensitive skin, or for maximizing the antimicrobial activity. Exemplary buffers include those based upon citric acid, boric acid, sodium carbonate and disodium phosphate, such as McIlvaine's Buffer (citric acid-phosphate) and Giffords, Buffer (boric acid-sodium carbonate). The incorporation of surfactants (e.g. "Pluronic ® F68 Surfactant", commercially available from BASF Corp., Parsippany, N. J.) modify the surface tension of the sealant compositions and enable them to wet catheter substrates which are usually made of low surface energy plastics, such as polytetrafluoroethylene, polyethylene, polypropylene and various silicones. As mentioned previously, surfactants can also be used to emulsify antimicrobials which are not soluble in the plasticizer. The additives may be added either to the polymer precursor, when the additive does not interfere with or is not affected by the polymerization, or may be added to the plasticizer or the polymerized medical sealant composition.

The polymerization of the polymer precursor is carried out by employing initiators which generate free-radicals upon the application of activating energy, such as that conventionally used in the polymerization of ethylenically unsaturated monomers. Included among useful free-radical initiators are the thermally activated initiators such as organic peroxides, organic hydroperoxides, and azo compounds. Representative examples of such initiators include benzoyl peroxide, tertiary-butyl perbenzoate, diisopropyl peroxydicarbonate, cumene hydroperoxide, azobis(isobutyronitrile), and the like. Generally, from about 0.1 to 5 percent by weight (based on the polymerizable components) of thermal initiator is used.

When thermally activated initiators are employed, the polymerization is carried out at between about 50° and 150° C. for about 0.1 to 5 hours, depending upon the temperature and the composition of the polymerizable composition. As is known in the art, polymerizations at temperatures as low as 0° C. can be carried out if suitable redox initiator catalysts are employed. Such redox initiator catalysts are listed in *Principles of Polymerization,* by George Odian, John Wiley and Sons (1981), pages 201-204.

The presently preferred initiators are activated photochemically. Such photochemically activated initiators are well known and have been described in the polymerization art, e.g., Chapter II of *Photochemistry* by Calvert and Pitts, John Wiley and Sons (1966) and in *Progress in Organic Coatings,* 13 (1985) 123–150. Representative examples of such initiators include acyloins and related compounds such as benzoin, benzoin methyl ether, benzoin ethyl ether, benzoin isopropyl ether, benzoin isobutyl ether, α-methylbenzoin, and 2-hydroxy-2-methyl-1-phenyl-1-propanone; ketone/amine combinations such as benzophenone/N-methyldiethanolamine, benzophenone/tributylamine and benzophenone/Michler's ketone; and benzilketals such as benzildimethylketal, benzildiethylketal and 2,5-dichlorobenzildimethylketal. A preferred photoinitiator is 2-hydroxy-2-methyl-1-phenyl-1-propanone Generally, the photoinitiator is used in amounts ranging from about 0.01 to 5 percent by weight of the polymerizable components. Preferably, about 0.02 to 2.0 percent by weight of photoinitiator is used.

When the activating energy is ultraviolet light, the irradiation is typically initiated at a temperature in the range of 0° to 50° C. for 0.5 minutes to 5 hours or more, depending upon the intensity of the radiation, the opacity and thickness of the polymerizable composition, and the identity and efficiency of the initiator.

There are several ways of preparing the medical sealant compositions of the present invention. The variations include polymerizing the polymer precursor in bulk or in solution with or without plasticizer and with or without an antimicrobial present. If no antimicrobial is present in the polymer precursor, it can be added to the solid polymer with or after the addition of the plasticizer.

Preferably, particularly where the composition is to be used as a caulkable sealant, it is prepared by the essentially solventless process of polymerizing a precursor comprising an N-vinyl lactam monomer, a crosslinker, and an initiator. Alternatively, a solvent can be added and then removed, e.g., by evaporation. Preferred solvents include glycerol, water, and mixtures thereof. Once completely cured, the polymer is ground into a fine powder having an average particle diameter of less than about 0.25 cm. Preferably the polymer is ground into a powder having an average particle diameter of between about 0.1 micron and 0.1 cm. Monomer residuals are then removed by either repeated emulsifications and precipitations in, respectively, water and acetone, or by a high vacuum at elevated temperatures, e.g., 100-150° C. The dried purified polymer is mixed with a plasticizer solution containing an antimicrobial. For compositions with relatively high polymer solids content, e.g. 30 percent, the plasticizer/antimicrobial solution will be completely absorbed in about 15 seconds. For low polymer solids content compositions, e.g. 2-5 percent, several hours are required for complete absorption of the plasticizer/antimicrobial solution.

Depending on the crosslink density and the percent by weight polymer solids in the compositions of the present invention, gels with a wide range of properties can be produced. These properties may range from tacky to non-tacky and from firm and cohesive to caulkable semifluids. For example, when the plasticizer is 80 percent by weight glycerol and 20 percent water and the concentration of 3,3′-ethylidene bis(N-vinyl-2-pyrrolidone) is 0.04 percent by weight of the polymer precursor, as the percent polymer solids increases from about 2.5 percent to about 30 percent, the cohesive strength of the composition varies between that of the plasticizer alone, and that of a marshmallow, or 3.5 (when measured according to the procedure of Examples 3–42); the tack of the composition varies between that of the plasticizer alone and that of "3M's Scotch ® brand Magic Mending Tape" (when measured by tactile perception); the stringiness of the composition varies between that of the plasticizer alone and 5 (measured according to the procedure of Examples 3–42); and the flow time (measured in time to extrude one milliliter of the composition thru a three millimeter diameter hole using an extrusion pressure of 775 g/1.8 cm$^2$) varies from about 0.1 second to 2000 seconds.

Likewise, where the plasticizer is 80 percent by weight glycerol in water, and the percent polymer solids is 30%, as the concentration of 3,3′-ethylidene bis(N-vinyl-2-pyrrolidone) increases from about zero to 1.28% by weight of the polymer precursor, the cohesive strength of the composition varies between that of the plasticizer alone and 3.5 (when measured according to the procedure of Examples 3–42); the tack of the composition varies between that of the plasticizer alone and that of 3M's "Scotch® brand Magic Mending Tape" (as measured by tactile perception); the stringiness of the composition varies between that of the plasticizer alone and 5 (as measured according to the procedure of Examples 3–42); and the flow time (measured in time to extrude one milliliter of the composition thru a three millimeter diameter hole using an extrusion pressure of 775 g/1.8 cm$^2$) varies from about 0.1 seconds to greater than about 4,000 seconds.

The properties of the compositions of the present invention are also affected by the amount of water in the plasticizer. For example, where the polymer matrix comprises 12.5 percent polymer solids and 0.16 percent by weight of the crosslinker 3,3'-ethylidene bis(N-vinyl-2-pyrrolidone), as the glycerol/water ratio varies from about 15:85 to 100 percent by weight glycerol, the cohesive strength of the composition varies between about 2 and 3.5; the tack of the composition varies between about 2 and 4; the stringiness of the composition varies between about 1 and 3; and the flow time varies from about 1.5 seconds to 2,300 seconds; when each of these properties is measured by the procedure described in Examples 3–42.

The compositions of the invention are highly moisture vapor transmissive. This property enables them to be advantageously employed as medical sealants for sealing a junction between living skin and a medical instrument penetrating the skin. Moisture from the body will not build-up under the surface of the sealant but will be transferred through the sealant to its surface. As mentioned previously, it is thought that the build-up of moisture under non-moisture vapor transmissive medical sealants, such as petroleum-based ointments, creates a beneficial environment for bacterial growth and a pathway for such bacteria to enter the penetrated skin.

It has been discovered, as illustrated in Example 101 that the moisture vapor transmission rate for a laminate comprising a layer of the sealant composition of the present invention and a layer of a segmented block polyester film (commercially available as "Hytrel® Film" from E. I. Dupont de Nemours Co., Wilmington, Del.) is in fact higher than the moisture vapor transmission rate of the layer of the "Hytrel® Film" alone. This effect is not expected and is difficult to explain. Typically the moisture vapor transmission rate (MVTR) of a two layer laminate of polymeric film and adhesive can be estimated with the following expression.

1/MVTR (Film) + 1/MVTR (Adhesive) = 1/MVTR (Laminate) The MVTR of a 0.0254mm thick "Hytrel® Film" is 1,830 g/m$^2$/24 hours. The MVTR of a 0.32 cm thick gel prepared according to Example 1 is 3,814 g/m$^2$/24 hours. Accordingly, a laminate of "Hytrel® Film" and the gel layer of Example 1 is calculated by the above formula to be 1,240 g/m$^2$/24 hours. However, when actually measured (see Example 99) the MVTR of the laminate was 2,680 g/m$^2$/24 hours; more than twice its calculated value. Apparently the compositions of the present invention increase the "Hytrel®Film's" affinity for water, thus, dramatically increasing the transmission of moisture through the laminate.

Another feature of the compositions of the present invention is that they are capable of incorporating a broad range of antimicrobials and are capable of providing effective and sustained activity of the antimicrobial for periods in excess of 72 hours. For purposes of contrast, acrylate polymer/antimicrobial combinations utilizing chlorhexidine gluconate and parachlorometaxylenol, made according to U.S. Pat. No. 4,310,509, are relatively inactive.

The compositions of the present invention can be utilized in a variety of medical applications. As previously mentioned, the medical sealant composition can be formulated so as to be useful as a caulkable sealant for sealing junctions between living skin and a medical instrument penetrating through the skin, such as a catheter. The compositions of this invention could also be utilized as a surgical skin prepping gel, or as a teat plug for preventing mastitis in cows. The gels of this invention when reinforced with an appropriate backing sheet, for example, plastic film such as polyester, polyethylene, woven or non-woven sheet made of natural or synthetic fibers, would find use as burn or wound dressings.

The following examples illustrate the medical sealant compositions of this invention. All parts are by weight unless otherwise noted. Examples 1–48 illustrate polymerization of the N-vinyl lactam, in solution (Examples 1 and 43) or in bulk conditions (Examples 2–42 and 44–48). Examples 49 and 50 illustrate polymerization of the N-vinyl lactam in the presence of the antimicrobial. Examples 51–80, and 91 illustrate addition of the antimicrobial to the powdered polymeric matrix. Examples 81–83, 92–96, 98 and 99 illustrate addition of the antimicrobial to the polymer gel. Examples 84–90 illustrate the use of additives. Example 97 and 100 illustrate the antimicrobial activity of the compositions of this invention. Examples 101 and 102 illustrate the high moisture vapor transmission rate (MVTR) of the compositions of this invention. Example 103 illustrates the adhesive properties of the compositions of this invention.

EXAMPLE 1

A mixture of 20 parts of N-vinyl-2-pyrrolidone, 0.2 parts of 2-hydroxy-2-methyl-1-phenyl-1-propanone, 0.032 parts of 3,3'-ethylidene bis(N-vinyl-2-pyrrolidone), 33.2 parts of glycerol and 8.4 parts of water was placed in a flat dish at a thickness of 1.3 cm and was irradiated through a 0.5 cm thick quartz plate with a broad spectrum 75 watt ultraviolet lamp commercially available as a "Sylvania® Sunlamp 052", from GTE Sylvania Inc., Manchester, N.H., at a distance of 40 cm for about 20 minutes until the product had gelled and was fully cured. The gel was soft, conformable and adhesive, as determined by tactile perception.

EXAMPLE 2

A mixture of 0.16 parts of 3,3'-ethylidene bis(N-vinyl-2-pyrrolidone), 1.0 parts of 2-hydroxy-2-methyl-1-phenyl-1-propanone and 100 parts of N-vinyl-2-pyrrolidone was placed in a flat dish at a thickness of 1.3 cm and was irradiated through a 0.5 cm thick quartz plate with a "Sylvania® Sunlamp 052" placed at a distance of 40 cm for about 20 minutes. The resultant solid polymeric poly(N-vinyl-2-pyrrolidone) product was ground into a powder of particle size less than 0.25 cm using a blender and then thrice both emulsified in water and reprecipitated in acetone to remove by-products and contaminants. The polymer was dried in a vacuum oven at 65° C. The polymer was then again ground into a fine powder using a grinder commercially available as a "Brinkham Retsch Grinder" from Brinkman Instruments Co., Westbury, N.Y. The grate was 1.0 mm and the grinder was used at 10,000 rpm to provide a particle size distribution of 850 microns and smaller.

EXAMPLES 3-42

These examples illustrate the effect of changing the amount of the crosslinker, 3,3'-ethylidene bis(N-vinyl-2-pyrrolidone) (EBVP) on the properties of the gels of this invention.

The reactants described in Table I with 1.0% by weight 2-hydroxy-2-methyl-1-phenyl-1-propanone were poured into round 8.9 cm diameter polyethylene trays at a depth of about 1.9 cm and irradiated with the broad spectrum ultraviolet lamp described in Example 1 for 20 minutes while purging with nitrogen gas. The gels obtained were removed from the trays, inverted and again irradiated with the same light source for 20 minutes. The discs of polymer obtained were ground using a mechanical blender to an average particle size of about 850 microns. From 2.5 to 30.0 percent by weight polymer was mixed with a solution of 80/20 ww glycerol/water using a spatula to provide 10 g samples. The percent gel swell, clarity, cohesive strength, flowability, tack and stringiness of each sample was evaluated and is recorded in Table I. Percent gel swell was measured by mixing from 2.5% to 30% by weight of powdered polymer of an average particle size of 850 microns in a solution of 80:20 ww glycerol/water to yield 20 gm total solution weight. The solutions were placed in 20 ml glass vials. The gels were allowed to settle to the bottom of the vials. The % gel swell is reported as the % volume of the solution that the swollen gel occupies. Cohesive strength was measured by pulling the plasticized gel apart by hand and assigning a number on a linear scale between 0 and 4 to the ease with which the gel was pulled apart. A value of 0 corresponded to the cohesive strength of a 80:20 percent by weight solution of glycerol in water. A value of 4 corresponded to the cohesive strength of a marshmallow. Flowability was measured by tactile perception and assigned a number on a scale of 0 for poorly deformable (i.e., recovers completely or substantially completely when deformed) to 5 for runny (i.e., equivalent to the flowability for 80:20 percent by weight solution of glycerol in water). Tack was measured by tactile perception and assigned a number on a scale of 1 for a tack equivalent to that of a 80:20 percent by weight solution of glycerol in water, to 5 for a tack equivalent to that of "Scotch® brand Magic Mending Tape", commercially available from 3M Co., St. Paul, MN. Stringiness, i.e., elongation observed before break, was measured by pulling 5 g of the gel apart by hand, and assigned a number on a scale of 1 to 5 to the length of the gel string before break. A stringiness of 1 was equivalent to that of a 80:20 percent by weight solution of glycerol in water. A stringiness of 2 meant that the elongation of the string before break was about 1.0 cm. A stringiness of 3 meant that the elongation of the string before break was about 2.5 cm. A stringiness of 4 meant that the elongation of the string before break was about 7.5 cm., and a stringiness of 5 meant that the elongation of the string before break was greater than 7.5 cm.

TABLE I

| | REACTANTS | | | | % Gel Swell (by volume) | | | | | | | | | | |
|---|---|---|---|---|---|---|---|---|---|---|---|---|---|---|---|
| Ex. | NVP[1] (Parts) | EBVP[2] (Parts) | Catalyst[3] (Parts) | % Solids (by wt.) | 15 Min | 30 Min | 1 Hr. | 2 Hr. | 24 Hr. | 6 Days | Gel Clarity[4] | Cohesive Strength | Flowability | Tack | Stringiness |
| 3 | 100 | 0 | 1.0 | 2.5 | 5 | 10 | 20 | 20 | 20 | 20 | 0 | 0 | 5 | 1.0 | 1.0 |
| 4 | 100 | 0 | 1.0 | 5.0 | 10 | 30 | 30 | 30 | 30 | 40 | 0 | 0 | 5 | 1.0 | 1.0 |
| 5 | 100 | 0 | 1.0 | 10.0 | 20 | 60 | 60 | 80 | 50 | 100 | 0 | 0.5 | 5 | 3.0 | 5.0 |
| 6 | 100 | 0 | 1.0 | 20.0 | 50 | 95 | 100 | 100 | 100 | 100 | 0 | 1.0 | 5 | 4.0 | 5.0 |
| 7 | 100 | 0 | 1.0 | 30.0 | 100 | 100 | 100 | 100 | 100 | 100 | 1 | 2.0 | 5 | 5.0 | 5.0 |
| 8 | 100 | 0.02 | 1.0 | 2.5 | 5 | 10 | 10 | 10 | 20 | 40 | 0 | 0 | 5 | 1.0 | 1.0 |
| 9 | 100 | 0.02 | 1.0 | 5.0 | 10 | 20 | 40 | 40 | 40 | 100 | 0 | 0.5 | 5 | 3.0 | 3.0 |
| 10 | 100 | 0.02 | 1.0 | 10.0 | 20 | 50 | 80 | 90 | 90 | 100 | 0 | 1.0 | 5 | 3.0 | 5.0 |
| 11 | 100 | 0.02 | 1.0 | 20.0 | 80 | 95 | 100 | 100 | 100 | 100 | 0 | 1.5 | 5 | 4.0 | 5.0 |
| 12 | 100 | 0.02 | 1.0 | 30.0 | 100 | 100 | 100 | 100 | 100 | 100 | 2 | 1.5 | 5 | 5.0 | 5.0 |
| 13 | 100 | 0.04 | 1.0 | 2.5 | 10 | 20 | 25 | 25 | 30 | 80 | 0 | 0 | 5 | 1.0 | 1.0 |
| 14 | 100 | 0.04 | 1.0 | 5.0 | 30 | 50 | 50 | 50 | 60 | 100 | 0 | 0 | 5 | 2.0 | 3.0 |
| 15 | 100 | 0.04 | 1.0 | 10.0 | 80 | 90 | 90 | 95 | 90 | 100 | 0 | 1.0 | 5 | 3.0 | 5.0 |
| 16 | 100 | 0.04 | 1.0 | 20.0 | 100 | 100 | 100 | 100 | 100 | 100 | 2 | 2.0 | 5 | 4.0 | 5.0 |
| 17 | 100 | 0.04 | 1.0 | 30.0 | 100 | 100 | 100 | 100 | 100 | 100 | 3 | 3.5 | 2 | 5.0 | 5.0 |
| 18 | 100 | 0.08 | 1.0 | 2.5 | 20 | 30 | 30 | 30 | 30 | 100 | 0 | 0.5 | 5 | 1.0 | 3.0 |
| 19 | 100 | 0.08 | 1.0 | 5.0 | 50 | 50 | 50 | 70 | 80 | 100 | 0 | 0.5 | 5 | 1.0 | 4.0 |
| 20 | 100 | 0.08 | 1.0 | 10.0 | 70 | 80 | 90 | 100 | 100 | 100 | 1 | 1.0 | 3 | 3.0 | 5.0 |
| 21 | 100 | 0.08 | 1.0 | 20.0 | 100 | 100 | 100 | 100 | 100 | 100 | 2 | 2.0 | 3 | 4.0 | 5.0 |
| 22 | 100 | 0.08 | 1.0 | 30.0 | 100 | 100 | 100 | 100 | 100 | 100 | 3 | 3.5 | 1 | 5.0 | 5.0 |
| 23 | 100 | 0.16 | 1.0 | 2.5 | 10 | 20 | 30 | 30 | 50 | 90 | 2 | 0 | 5 | 1.0 | 1.0 |
| 24 | 100 | 0.16 | 1.0 | 5.0 | 50 | 80 | 100 | 100 | 100 | 100 | 2 | 0 | 5 | 2.0 | 2.0 |
| 25 | 100 | 0.16 | 1.0 | 10.0 | 100 | 100 | 100 | 100 | 100 | 100 | 2 | 0.5 | 2 | 3.0 | 2.0 |
| 26 | 100 | 0.16 | 1.0 | 20.0 | 100 | 100 | 100 | 100 | 100 | 100 | 2 | 2.0 | 1 | 4.0 | 2.5 |
| 27 | 100 | 0.16 | 1.0 | 30.0 | 100 | 100 | 100 | 100 | 100 | 100 | 3 | 3.5 | 1 | 4.5 | 2.5 |
| 28 | 100 | 0.32 | 1.0 | 2.5 | 10 | 20 | 30 | 30 | 40 | 80 | 2 | 0 | 5 | 1.0 | 1.0 |
| 29 | 100 | 0.32 | 1.0 | 5.0 | 50 | 80 | 90 | 100 | 100 | 100 | 2 | 0 | 5 | 1.0 | 1.0 |
| 30 | 100 | 0.32 | 1.0 | 10.0 | 100 | 100 | 100 | 100 | 100 | 100 | 2 | 0.5 | 2 | 2.0 | 1.0 |
| 31 | 100 | 0.32 | 1.0 | 20.0 | 100 | 100 | 100 | 100 | 100 | 100 | 3 | 1.0 | 1 | 3.0 | 1.0 |
| 32 | 100 | 0.32 | 1.0 | 30.0 | 100 | 100 | 100 | 100 | 100 | 100 | 3 | 1.0 | 0 | 3.0 | 1.0 |
| 33 | 100 | 0.64 | 1.0 | 2.5 | 20 | 20 | 20 | 20 | 30 | 30 | 2 | 0 | 5 | 1.0 | 1.0 |
| 34 | 100 | 0.64 | 1.0 | 5.0 | 40 | 40 | 40 | 80 | 90 | 90 | 2 | 0 | 5 | 1.0 | 1.0 |
| 35 | 100 | 0.64 | 1.0 | 10.0 | 100 | 100 | 100 | 100 | 100 | 100 | 2 | 0 | 2 | 1.0 | 1.0 |
| 36 | 100 | 0.64 | 1.0 | 20.0 | 100 | 100 | 100 | 100 | 100 | 100 | 3 | 0.5 | 1 | 1.5 | 1.0 |
| 37 | 100 | 0.64 | 1.0 | 30.0 | 100 | 100 | 100 | 100 | 100 | 100 | 3 | 0.5 | 0 | 1.0 | 1.0 |
| 38 | 100 | 1.28 | 1.0 | 2.5 | 20 | 20 | 20 | 20 | 30 | 20 | 2 | 0 | 5 | 1.0 | 1.0 |
| 39 | 100 | 1.28 | 1.0 | 5.0 | 30 | 30 | 40 | 50 | 70 | 70 | 2 | 0 | 5 | 1.0 | 1.0 |
| 40 | 100 | 1.28 | 1.0 | 10.0 | 60 | 70 | 80 | 90 | 100 | 100 | 2 | 0 | 2 | 1.0 | 1.0 |
| 41 | 100 | 1.28 | 1.0 | 20.0 | 10 | 100 | 100 | 100 | 100 | 100 | 3 | 0 | 1 | 1.0 | 1.0 |

TABLE I-continued

| | REACTANTS | | | | % Gel Swell (by volume) | | | | | | | | | | |
|---|---|---|---|---|---|---|---|---|---|---|---|---|---|---|---|
| Ex. | NVP[1] (Parts) | EBVP[2] (Parts) | Catalyst[3] (Parts) | % Solids (by wt.) | 15 Min | 30 Min | 1 Hr. | 2 Hr. | 24 Hr. | 6 Days | Gel Clarity[4] | Cohesive Strength | Flow-ability | Tack | String-iness |
| 42 | 100 | 1.28 | 1.0 | 30.0 | 100 | 100 | 100 | 100 | 100 | 100 | 3 | 0 | 0 | 1.0 | 1.0 |

[1] parts by weight N-vinyl-2-pyrrolidone
[2] parts by weight 3,3'-ethylidene bis(N-vinyl-2-pyrrolidone)
[3] parts by weight 2-hydroxy-2-methyl-1-phenyl-1-propanone
[4] 0 = clear, 1 = slightly translucent; 2 = translucent, 3 = opaque The desired properties of the gels for purposes of this invention are 100% gel swell, slight to high cohesive strength (values of 1–4), very flowable to deformable, (values of 1–5), slight to very tacky (values of 3–5) and slight to no stringiness (values 1–3). The optimal choice of these properties will depend on the desired application. For example, the compositions of Examples 25, 26, 27, 31 and 32 would be particularly useful as catheter sealants, once formulated with an antimicrobial. The composition of Examples 25 and 30 would have use as caulkable catheter sealants. The compositions of Examples 17 and 22 would be useful as teat plugs. The compositions of Examples 25, 26, 27, 31 and 32 when utilized with an appropriate backing and formulated with an antimicrobial would have use as wound or burn dressings.

Table I shows that the swelling capacity of the crosslinked polymer had an optimum at 0.08%, 3,3'-ethylidene bis(N-vinyl-2-pyrrolidone); that tack increased with percent polymer solids and decreased with crosslinker concentration; flow decreased with percent polymer solids and increased with decreasing crosslinker concentration; stringiness increased with percent polymer solids and decreased with increasing crosslinker concentration; cohesive strength had an optimum at 0.04–0.16 percent EBVP, decreased with higher and lower EBVP concentrations and increased with percent polymer solids.

EXAMPLE 43

In a comparative set of experiments the formulations of Table I were polymerized in solution with 33.2 parts of glycerol and 8.4 parts of water, according to the procedure of Example 1. The cured gels showed the same trend of properties as is recorded in Table 1, except that approximately twice as much crosslinker was required to obtain similar properties.

EXAMPLE 44

A mixture of 10 g of N-vinyl-2-caprolactam, 16 mg of 3,3'-ethylidene bis(N-vinyl-2-pyrrolidone) and 100 mg of 2-hydroxy-2-methyl-1-phenyl-1-propanone was heated at 49° C. for one hour, poured into a polyethylene dish to a depth of 1.5 cm and photolyzed for 20 minutes with the ultraviolet light source described in Example 1 while it was flushed with nitrogen gas and maintained under nitrogen. The clear polymer was separated and ground by a mechanical blender into a fine white powder having an average particle size of approximately 850 microns.

EXAMPLE 45

A mixture of 9.0 g of N-vinyl-2-pyrrolidone, 20 mg of adipic acid divinyl ester, 1.0 g of 2-hydroxyethyl methacrylate and 100 mg of 2-hydroxy-2-methyl-1-phenyl-1-propanone was poured into a polyethylene dish to a depth of 1.5 cm and photolyzed with the ultraviolet light source of Example 1 for 20 minutes at a distance of 40 cm while it was purged continuously with nitrogen gas. The clear polymer was separated and ground by a mechanical blender into a fine white powder having an average particle size of approximately 850 microns.

EXAMPLE 46

A mixture of 7.5 g of N-vinyl-2-pyrrolidone, 20 mg of 3,3'-ethylidene bis(N-vinyl-2-pyrrolidone), 2.5 g of 2-hydroxyethyl methacrylate, and 0.10 g of 2-hydroxy-2-methyl-1-phenyl-1-propanone was reacted as described in Example 45. The clear polymer was ground by a mechanical blender into a fine white powder having an average particle size of approximately 850 microns.

EXAMPLE 47

A mixture of 5.0 g of N-vinyl-2-pyrrolidone, 100 mg of 2-hydroxy-2-methyl-1-phenyl-1-propanone, 5.0 g of 2-hydroxyethyl methacrylate and 20 mg of adipic acid divinyl ester was reacted as described in Example 45. The clear polymer was separated and ground by a mechanical blender into a fine white powder having an average particle size of approximately 850 microns.

EXAMPLE 48

A mixture of 30 g of N-vinyl-2-pyrrolidone, 60 mg of 3,3'-ethylidene bis(N-vinyl-2-pyrrolidone) and 120 mg of tertiary-butyl peroxide was flushed with nitrogen gas, maintained under nitrogen and heated at 100° C. for 30 minutes, then at about 113° C. for two hours. The polymer was separated and ground by a mechanical blender into a powder having an average particle size of approximately 850 microns.

EXAMPLE 49

Mixtures of 8.3 parts glycerol, 2.1 parts of a solution of 20 percent by weight chlorhexidine gluconate in water, 5.0 parts of N-vinyl-2-pyrrolidone, 0.05 parts of 2-hydroxy-2-methyl-1-phenyl-1-propanone and 0.004, 0.008 or 0.016 parts of 3 3'-thylidene bis(N-vinyl-2-pyrrolidone) respectively, was irradiated with the ultraviolet light source of Example 1 at a distance of 40 cm through a 0.5 cm quartz plate for about 20 minutes. The polymer layers were about 3 mm thick and were in each case soft, conformable gels with good adhesive characteristics. As the concentration of 3,3'-ethylidene bis (N-vinyl-2-pyrrolidone) increased, the resistance to flow of the resulting gel increased according to tactile perception.

EXAMPLE 50

Mixtures of 8.3 parts of glycerol, 2.1 parts of water, 5.0 parts of N-vinyl-2-pyrrolidone, 0.05 parts of 2-hydroxy-2-methyl-1-phenyl-1-propanone, 0.077 parts of parachlorometaxylenol and 0.004, 0.008 or 0.016 parts of 3,3,'-ethylidene bis(N-vinyl-2-pyrrolidone), respectively were irradiated with the ultraviolet lamp of Example 1 at a distance of 40 cm through a 0.5 cm quartz plate for about 20 minutes. The polymer layers were about 3 mm thick and were in each case soft, conformable gels with good adhesive characteristics. As the concentration of 3,3'-ethylidene bis(N-vinyl-2-pyrrolidone) increased, the resistance to flow of the gel increased as measured by tactile perception.

EXAMPLE 51

To 1.0 part of a solution of 20 parts of iodine and 24 parts of sodium iodide in 56 parts of glycerol, 4.47 parts of glycerol and 3 72 parts of water was added 1 25 parts of the powdered polymer of Example 2, followed by thorough mixing. Within 5 minutes a plasticized gel was obtained. This gel is particularly useful as a catheter sealant.

EXAMPLES 52–75

Using powdered polymer obtained in Example 2, a series of gels was obtained by varying the amount of polymer in the gel, the glycerol-water ratio and the percent iodine and sodium iodide present. The iodine:sodium iodide ratio was maintained at 20:24. The properties of these gels are recorded in Table II.

Cohesive strength, flowability, tack and stringiness were measured according to the procedure described in Examples 3–42. Flow time was the time in seconds to extrude one milliliter of gel through a three millimeter diameter hole in a polypropylene sheet 8 millimeters thick using an extrusion pressure of 775 grams per 1.8 cm².

of Examples 57, 60–64, 68–70, 74 and 75 would be useful as caulkable catheter sealants.

EXAMPLE 76

A gel was prepared by blending 12.5 parts of the polymer of Example 48 with 70 parts of glycerol and 17.5 parts of water. After standing for about 16 hours at 20° C., the properties of the gel were evaluated and assigned a number, as in Examples 3–42.
Tackiness: 3
Cohesiveness: 3
Stringiness: 1
Flowability: 4

If an antimicrobial were added, this gel would be particularly useful as a catheter sealant.

EXAMPLE 77

A gel was prepared by blending 2.0 g of the polymer of Example 44 with 0.50 g of a solution of 20% by wt. chlorhexidine gluconate in water, 0.75 g of glycerol and 1.75 g of water. After standing for about 16 hours at 20° C., the properties of the gel were evaluated and assigned a number as in Examples 3–42.
Tackiness: 4
Cohesiveness 3
Stringiness: 2
Flowability: 1

This gel is particularly useful as a catheter sealant

TABLE II

| | COMPONENTS | | | PROPERTIES MEASURED | | | | |
| --- | --- | --- | --- | --- | --- | --- | --- | --- |
| Ex. | Polymer (Weight %) | Glycerol Water Ratio | Iodine (Weight %) | Cohesive Strength | Flow | Tack | Stringiness | Flow Time (Sec.) |
| 52 | 7.2 | 27.5/82.5 | 0.72 | 1 | 5 | 1 | 1 | 0.1 |
| 53 | 17.8 | 27.5/82.5 | 0.72 | 3 | 4 | 2 | 1 | 5.0 |
| 54 | 7.2 | 87.5/12.5 | 0.72 | 3 | 4 | 2 | 1 | 478.0 |
| 55 | 17.8 | 87.5/12.5 | 0.72 | 4 | 2 | 4 | 4 | 1903.0 |
| 56 | 7.2 | 27.5/82.5 | 1.78 | 1 | 5 | 1 | 1 | 0.1 |
| 57 | 17.8 | 27.5/82.5 | 1.78 | 3 | 3 | 3 | 2 | 16.0 |
| 58 | 7.2 | 87.5/12.5 | 1.78 | 3 | 4 | 2 | 1 | 0.5 |
| 59 | 17.8 | 87.5/12.5 | 1.78 | 4 | 2 | 4 | 3 | 3855.0 |
| 60 | 12.5 | 57.5/42.5 | 1.25 | 3 | 4 | 2 | 1 | 8.0 |
| 61 | 12.5 | 57.5/42.5 | 1.25 | 3 | 4 | 2 | 1 | 8.0 |
| 62 | 12.5 | 57.5/42.5 | 1.25 | 3 | 3 | 3 | 2 | 9.0 |
| 63 | 12.5 | 57.5/42.5 | 1.25 | 3 | 3 | 3 | 2 | 10.0 |
| 64 | 20.0 | 57.5/42.5 | 1.25 | 3 | 2 | 4 | 3 | 607.0 |
| 65 | 5.0 | 57.5/42.5 | 1.25 | 1 | 5 | 2 | 1 | 0.1 |
| 66 | 12.5 | 100/0 | 1.25 | 4 | 2 | 5 | 3 | 1977.0 |
| 67 | 12.5 | 15/85 | 1.25 | 2 | 4 | 2 | 1 | 2.0 |
| 68 | 12.5 | 57.5/42.5 | 2.0 | 2 | 4 | 3 | 2 | 394.0 |
| 69 | 12.5 | 57.5/42.5 | 0.5 | 2 | 4 | 2 | 1 | 4.0 |
| 70 | 20.0 | 57.5/42.5 | 1.25 | 3 | 2 | 4 | 3 | 577.0 |
| 71 | 5.0 | 57.5/42.5 | 1.25 | 1 | 5 | 1 | 1 | 0.1 |
| 72 | 12.5 | 100/0 | 1.25 | 3 | 2 | 3 | 3 | 2591.0 |
| 73 | 12.5 | 15/85 | 1.25 | 2 | 4 | 2 | 1 | 1.0 |
| 74 | 12.5 | 57.5/42.5 | 2.0 | 2 | 4 | 3 | 2 | 410.0 |
| 75 | 12.5 | 57.5/42.5 | 0.5 | 3 | 4 | 3 | 2 | 4.0 |

Table II illustrates that as the percent polymer solids increases, cohesive strength increases, tack increases, stringiness increases, flow time increases and flow decreases. As the glycerol/water ratio increases, cohesive strength increases, tack and stringiness increase, flow decreases and flow time increases. The change in percent iodine does not have much effect in the range observed. The compositions of the present invention can be formulated so as to have a wide range of physical properties, thus making the compositions of this invention useful in a wide range of medical applications. The compositions of Examples 59, 66 and 72 would be particularly useful as catheter sealants. The compositions

EXAMPLE 78

A gel was prepared by blending 1.0 g of the polymer of Example 45 with 0.1 g of iodine and 0.2 g of sodium iodide premixed with 2.06 g of glycerol and 1.64 g of water. After standing for about 16 hours at 20° C., the properties of the gel were evaluated and assigned a number as in Examples 3–42
Tackiness: 5
Cohesiveness: 4
Stringiness: 2
Flowability: 1

This gel is particularly useful as a catheter sealant.

EXAMPLE 79

A gel was prepared by blending 1.0 g of the polymer of Example 46 with 0.1 g of iodine and 0.2 g of sodium iodide premixed in 2.06 g of glycerol and 1.64 g of water. After standing for about 16 hours at 20° C., the properties of the gel were evaluated and assigned a number as in Examples 3-42.
Tackiness: 3
Cohesiveness: 1
Stringiness: 1
Flowability: 1
This gel is particularly useful as a catheter as a sealant.

EXAMPLE 80

A gel was prepared by blending 2.0 g of the polymer of Example 47 with 0.1 g of iodine and 0.2 g of sodium iodide premixed with 1.56 g of glycerol and 1.14 g of water. After standing for about 16 hours at 20° C., the properties of the gel were evaluated and assigned a number as in Examples 3-42.
Tackiness: 3
Cohesiveness: 3
Stringiness: 1
Flowability: 1
This gel is particularly useful as a catheter sealant.

EXAMPLE 81

A square (2.54 cm×2.54 cm×0.32 cm) of the gel of Example 1 was soaked for four hours in excess water, then soaked for four hours in 100 parts acetone per part of gel. This soaking procedure was repeated three times. The gel was then dried and placed in a solution of 159.6 parts of glycerol, 40.4 parts of water, 2.4 parts of sodium iodide and 2.0 parts of iodine for 24 hours. The resulting gel contained 2 percent iodine. The gel was soft, conformable and adhesive. This gel is particularly useful as a catheter sealant.

EXAMPLE 82

A square (2.54 cm×2.54 cm×0.32 cm) of the gel of Example 1 was acetone washed and dried for three hours in an oven at 65° C. The gel was then soaked for 24 hours in a solution of 79.8 parts of glycerol and 20.2 parts of 20 percent chlorhexidine gluconate in water. The gel was soft, conformable and adhesive This gel is particularly useful as a catheter sealant or a teat plug for cows.

EXAMPLE 83

Three square gel pieces 2.54 cm by 2.54 cm by 3 mm thick were prepared according to the procedure of Example 1, and acetone washed and dried The gels were soaked for 24 hours in a solution containing 13.4 g of water, 52.9 g of glycerol, 0.5 g of neomycin sulfate, 40,000 U.S P. units of bacitracin and 500,000 units of polymyxin B sulfate. Excess solution was then wiped away. The gels obtained were soft, conformable and adhesive.

This gel is particularly useful as a teat plug for cows or a catheter sealant

EXAMPLE 84

To a solution of 69.1 parts of glycerol, 18.3 parts of water, 2.12 parts of iodine, 4.25 parts of sodium iodide, 0.52 parts of citric acid and 1.37 parts of disodium hydrogen phosphate, was added 12.5 parts of powdered polymer prepared according to Example 2 followed by thorough mixing. This procedure provided a gel with a pH value of 6.2. This gel is particularly useful as a catheter sealant.

EXAMPLE 85-90

A series of gels was prepared which included a surfactant at various levels. The gels were prepared from 7 parts of glycerol, 1.75 parts of water, 1.25 parts of the polymer of Example 2 and a polyoxypropylene-polyoxyethylene block copolymer, commercially available as "Pluronic ® F-68 Surfactant" from BASF Corp., Parsippany, N.J.

The adhesive shear strength of these gels to a silicone rubber (commercially available as "Dow Corning Silastic ® Silicone Rubber MD/GR VUL/NR-020" from Dow Corning Corp., Hemlock, MI.) was evaluated using a variation of ASTM method D3164-73 (incorporated herein by reference) wherein the jaw speed of the Instron (Model 1122) was 12.7 cm/min and the overlap of the gel film was 3.2 cm$^2$. The results are reported in Table III.

TABLE III

| Example No. | % "Pluronic ® F-68 Surfactant" (by wt.) | Shear Strength (kg) |
| --- | --- | --- |
| 85 | 0 | 0.91 |
| 86 | 0.1 | 1.26 |
| 87 | 0.5 | 1.57 |
| 88 | 1.0 | 1.34 |
| 89 | 5.0 | 1.52 |
| 90 | 10.0 | 1.75 |

EXAMPLE 91

2.5 g of the polymer of Example 2, was swollen with 5.25 g of isopropanol and 2.25 g of deionized water to provide an adhesive gel. The isopropanol serves as an antimicrobial agent as well as a plasticizer. The mixture was very adhesive and transparent. It has particular utility as a fast skin prepping dressing.

EXAMPLE 92

2.0 cm$^3$ of the polymer gel film of Example 1 was soaked for 24 hours in 79.8 parts glycerol and 20.2 parts of a solution of 20% by wt. chlorhexidine gluconate in water.

EXAMPLE 93 2.0 cm$^3$ of the polymer gel film of Example 1 was soaked for 24 hours in 20.2 parts water, 79.8 parts glycerol, 4.7 parts parachlorometaxylenol, and 0.4 parts ethylenediaminetetraacetic acid.

EXAMPLE 94

2.0 cm$^3$ of the polymer gel film of Example 1 was soaked for 24 hours in 40.4 parts water, 159.6 parts glycerol, 0.6 parts sodium iodide and 2.0 parts iodine.

EXAMPLE 95

2.0 cm$^3$ of the polymer gel film of Example 1 was soaked for 24 hours in 40.4 parts water, 159.6 parts glycerol, 2.4 parts sodium iodide and 2.0 parts iodine.

EXAMPLE 96

2.0 cm$^3$ of the polymer gel film of Example 1 was soaked for 24 hours in 13.4 g water, 52.9 g glycerol, 0.5 g neomycin sulfate, 40,000 units zinc bacitracin and 500,000 units polymyxin B sulfate.

EXAMPLE 97

Five antimicrobial gels of the invention were used to evaluate antimicrobial activity. A standard containing no antimicrobial agent was prepared by soaking 2.0 cm$^3$ of the polymer gel of Example 1 in 79.8 parts glycerol and 20.2 parts water for 24 hours. An in vitro test, the Ulrich Procedure (Infection in Surgery, Aug., 1984, 569–574), incorporated herein by reference, for evaluating antimicrobial activity versus Staphylococcus aureus No. 319 with a 90 minute exposure was used. The results are shown in Table IV.

TABLE IV

| Example | Activity | % Kill |
| --- | --- | --- |
| Standard | Not Active | 0 |
| 92 | 6 Log Reduction | 99.9999 |
| 93 | 6 Log Reduction | 99.9999 |
| 94 | 6 Log Reduction | 99.9999 |
| 95 | 6 Log Reduction | 99.9999 |
| 96 | 6 Log Reduction | 99.9999 |

Table IV illustrates that the compositions of the invention (Examples 92–96) killed virtually all bacteria present.

EXAMPLE 98

2.0 cm$^3$ of the gel film of Example 1 was soaked for 24 hours in 40.4 parts water, 159.6 parts glycerol, 2.6 parts iodine and 4.8 parts of sodium iodide.

Example 99

2.0 cm$^3$ of the gel film of Example 1 was soaked for 24 hours in 70.67 parts water, 279.33 parts glycerol, 2.10 parts parachlorometaxylenol and 0.88 parts ethylenediaminetetraacetic acid.

EXAMPLE 100

The in-vivo antimicrobial activity of the gels of Examples 92, 95, 96, 98 and 99 was measured. The test method required the placement of each formulation on the backs of three subjects, who had been screened for high bacteria counts (greater than 3 logs), for a period of three days using the Williamson and Klugman scrub cup technique (J. Invest. Dermatol. 72, 165–170), incorporated herein by reference. Following this time the formulations were removed, residual antimicrobial agent neutralized, and the viable bacteria were removed and counted by the Williamson and Klugman scrub cup technique. The results are presented as an average of 6 replicates in Table V along with bacterial counts for certain known antimicrobial formulations.

TABLE V

| Example | Antimicrobial (% by wt.) | Log Reduction | % Kill |
| --- | --- | --- | --- |
| 92 | 2.8% Chlorhexidine Gluconate | 1.53 | 97.0 |
| 95 | 1.1% Iodine 1.2% Sodium Iodide | 1.80 | 98.4 |
| 96 | Neomycin Sulfate/ Zinc Bacitracin/ Polymyxin B Sulfate[3] | 2.19 | 99.4 |
| 98 | 1.3% Iodine 2.4% Sodium Iodide | 1.99 | 99.1 |
| 99 | 0.4% PCMX[1] 0.17% EDTA[2] | 1.13 | 92.6 |
| Efodine ® ointment[4] | 1% Iodine | 0.91 | 87.7 |
| Tegaderm ® Plus Transparent | 2% Iodine 2.4% Sodium Iodide | 0.77 | 83.0 |
| IV Dressing[5] | | | |
| Neosporin Ointment[6] | Neomycin Sulfate Zinc Bacitracin Polymyxin B Sulfate[3] | −0.20 | Regrowth (+58.5) |

[1]Parachlorometaxylenol
[2]Ethylenediaminetetraacetic Acid
[3]In a concentration sufficient to provide that each gram of gel contains 5 mg neomyoin sulfate, 400 units zinc bacitracin and 5,000 units polymyxin B sulfate.
[4]commercially available from Fougera and Co., Melville, N.Y.
[5]commercially available from 3M Co., St. Paul, MN.
[6]commercially available from Burroughs Wellcome Co., Research Triangle Park, N.C.

EXAMPLE 101

This example illustrates the high moisture vapor transmission rates (MVTR) of the gels of this invention. The MVTR for the gel of Example 1 was compared with the MVTR for a segmented block polyester film, commercially available as "Hytrel ® Film 4056" from Dupont de Nemours Co., Wilmington, Del., alone and laminated to an acrylate adhesive or the film of Example 1.

The MVTR for each film was determined by using a variation of ASTM method E 96-80, incorporated herein by reference. The film was placed adhesive side down over the opening of a standard glass vessel half filled with deionized water.

The MVTR was determined by measuring by weight loss of the vessel after 24 hours, at 41° C. and 10% ambient relative humidity. The results are reported in Table VI. The gel of Example 1 had a very high MVTR (3800 g/m$^2$/24 hr). Note that the MVTR for the laminate of the gel of Example 1"Hytrel ® Film" (2680 g/m$^2$/24 hrs) was higher than for the "Hytrel ® Film" alone (1830 g/m$^2$/24 hr). This effect was not expected. Apparently the gels of this invention surprisingly increase the "Hytrel ® Films" affinity for water.

TABLE VI

| Composition | MVTR (g/m$^2$/24 hr) @ 90% R.H. + 41° C. |
| --- | --- |
| Example 1 (0.32 cm) | 3,814 |
| Hytrel ® Film 4056 (.0254 mm) | 1,833 |
| Hytrel ® Film 4056 (0.254 mm) + Acrylate Adhesive[1] (0.0762 mm) | 379 |
| Hytrel ® Film 4056 (0.254 mm) Example 1 (0.32 cm) | 2,684 |

[1]a copolymer of 91% by wt. isooctyl acrylate and 9% by wt. N-vinyl-2-pyrrolidone

EXAMPLE 102

A mixture containing 12.5 g of the polymer of Example 2, 17.22 g of distilled water, 68.9 g of glycerol, 0.50 g of neomycin sulfate, 40,000 units (0.619 g) of zinc bacitracin and 500,000 units of polymyxin B sulfate was prepared. The mixture was placed on a 1 mil (0.0254 mm) film of "Hytrel ® Film 4056" and covered with a silicone-coated paper release liner (commercially available as "Nat. 20 mg 10/10 IT/0", from Akrosil, Menasha, WI.) to form a laminate. The laminate was flattened using a hydraulic press to a thickness of 0.16 cm. The release liner was removed and the exposed gel was quite adhesive as determined by tactile perception. THe moisture vapor transmission rate of the laminate was about 2600 g/m²/24 hour, when measured in accordance with the procedure of Example 99. This laminate would have use as a wound or burn dressing.

EXAMPLE 103

This example illustrates the adhesive properties of several compositions of this invention.

T-Peel tests were performed on each sample by using a variation of ASTM D 1876, incorporated herein by reference. The samples were tested at an adhesive thickness of 1 mm and conditioned for 2 hours at room temperature. T-Peel was measured on a relatively easy to stick to surface, aluminum foil (75.4 g/cm), and a difficult to stick to surface, low density polyethylene (16.4 g/cm). The results of the T-Peel tests are reported in Table VII. Table VII also illustrates the performance of "Scotch ® brand Magic Mending Tape", commercially available from 3M, St. Paul, Mn.

TABLE VII

| | COMPOSITION | | T-PEEL | |
|---|---|---|---|---|
| Example No. | Percent Polymer Solids (by wt.) | EBVP[1] | On Polyethylene[2] (g/cm) | On Aluminum Foil[3] (g/cm) |
| 5 | 10.0 | 0.0 | 0.0 | 0.0 |
| 7 | 30.0 | 0.0 | 0.0 | 0.0 |
| 10 | 10.0 | 0.02 | 0.0 | 0.0 |
| 12 | 30.0 | 0.02 | 14.3 | 11.8 |
| 15 | 10.0 | 0.04 | 0.0 | 0.0 |
| 17 | 30.0 | 0.04 | 35.7 | 33.2 |
| 20 | 10.0 | 0.08 | 3.2 | 4.1 |
| 22 | 30.0 | 0.08 | 55.9 | 43.2 |
| 25 | 10.0 | 0.16 | 3.9 | 3.2 |
| 27 | 30.0 | 0.16 | 50.5 | 52.7 |
| 30 | 10.0 | 0.32 | 2.9 | 3.2 |
| 32 | 30.0 | 0.32 | 4.5 | 5.2 |
| 35 | 10.0 | 0.64 | 2.7 | 4.6 |
| 37 | 30.0 | 0.64 | 5.0 | 5.5 |
| 40 | 10.0 | 1.28 | 2.1 | 2.3 |
| 42 | 30.0 | 1.28 | 2.7 | 2.5 |
| 3M's "Scotch ® brand Magic Mending Tape" | — | — | 16.4 | 75.4 |

[1]3,3'-ethylidene bis(N-vinyl-2-pyrrolidone) expressed as percent by weight of monomer
[2]0.12 mm (4.6 mil) low density polyethylene, commercially available from Enron Chemical Co., Morris, Ill., as resin "NPE 963-2"
[3]0.10 mm (3.9 mil) aluminum foil The gels of the invention show remarkable adhesion to both types of surfaces, with an optimum at 0.08 to 0.16 percent EBVP. It is very surprising that the hydrophilic adhesives of this invention adhere so well to a hydrophobic surface such as polyethylene.

What is claimed is:

1. A medical sealant composition comprising:
   (a) a crosslinked, swellable polymeric matrix formed by a free-radical polymerization of at least one polymerizable monomeric species wherein at least 50 percent by weight of the monomeric component is comprised of one or more N-vinyl lactams, and a crosslinker which is a multi-ethylenically unsaturated compound with the ethylenic groups being vinyl, allyl, or methallyl groups bonded to nitrogen or oxygen atoms, said N-vinyl lactam monomer being present in a concentration of about 5 to 99.9 percent by weight of the polymeric matrix precursor and said crosslinker being present in a concentration of about 0.02 to 5.0 percent by weight of said N-vinyl lactam monomer;
   (b) a plasticizing solution present in a concentration of between about 55 and less than about 95 percent by weight of said medical sealant composition; and
   (c) an antimicrobial present in a concentration of between about 0.01 and 10 percent by weight of said medical sealant composition;
   which composition is formulated so as to have a T-Peel value of at least about 3 g/cm when measured on low density polyethylene, as described herein.

2. A composition in accordance with claim 1 wherein said multi-ethylenically unsaturated compound is selected from the group consisting of divinyl, diallyl and dimethallyl esters; divinyl, diallyl and dimethallyl amides; divinyl, diallyl and dimethallyl ethers; and divinyl, diallyl and dimethallyl ureas.

3. A composition in accordance with claim 1 wherein said multi-ethylenically unsaturated compound is a divinyl amide or a divinyl urea in an amount of from about 0.02 to about 0.5 percent by weight of said monomeric species.

4. A composition in accordance with claim 1 wherein said multi-ethylenically unsaturated compound is a divinyl, diallyl or dimethallyl ester; a diallyl or dimethallyl ether; a diallyl or dimethallyl amide; or a diallyl or dimethallyl urea in an amount of from about 0.05 to about 2 percent by weight of said monomeric species.

5. A composition in accordance with claim 1 wherein said multi-ethylenically unsaturated compound is a divinyl ether in an amount of from about 0.5 to about 5 percent by weight of said monomeric species.

6. A composition in accordance with claim 1 wherein the N-vinyl lactam monomer is N-vinyl-2-pyrrolidone.

7. A composition in accordance with claim 1 wherein said plasticizer is comprised of about 10 to 80 percent by weight glycerol in water.

8. A composition in accordance with claim 1 wherein said antimicrobial is selected from the group consisting of iodine, chlorhexidine gluconate, parachlorometaxylenol, zinc bacitracin, neomycin sulfate and polymyxin B sulfate.

9. A composition in accordance with claim 8 wherein said antimicrobial is iodine.

10. A composition in accordance with claim 1 wherein said polymeric matrix includes a polymerizable monomeric species selected from the group consisting of hydroxyalkyl acrylates and methacrylates; water soluble amines; water soluble hydrazine derivatives; and mono-olefinic sulfonic acids and their salts.

11. A method of preparing a medical sealant composition, comprising the steps of
   (a) preparing a mixture comprising at least one polymerizable monomeric species, and a crosslinker which is a multiethylenically unsaturated compound wherein the ethylenic groups are vinyl groups, allyl groups, or methallyl groups bonded to nitrogen or oxygen atoms, wherein at least 50 percent by weight of the monomeric component is comprised of one or more N-vinyl lactams and said crosslinker is present in a concentration of about 0.02 to 5.0 percent by weight of said N-vinyl lactam monomer;
   (b) exposing said composition to sufficient energy to result in the formation of a crosslinked swellable polymeric matrix;
   (c) grinding said polymer into a powder having an average particle size of less than about 0.25 cm;
   (d) adding said powder to a plasticizer solution having an antimicrobial therein, said plasticizing solution being present in a concentration of between about 55 and less than about 95 percent by weight of said medical sealant composition, said antimicrobial being present in a concentration of between about 0.01 and 10 percent by weight of said medical sealant composition and said powder, plasticizing solution and antimicrobial being present in a concentration sufficient to provide said medical sealant composition with a T-Peel value of at least about 3 g/cm when measured on low density polyethylene, as described herein.

12. A method of preparing a medical sealant composition, comprising the steps of
   (a) preparing a mixture comprising at least one polymerizable monomeric species, and a crosslinker which is a multiethylenically unsaturated compound wherein the ethylenic groups are vinyl groups, allyl groups, or methallyl groups bonded to nitrogen or oxygen atoms, and an antimicrobial, wherein at least 50 percent by weight of the monomeric component is comprised of one or more N-vinyl lactams and said crosslinker is present in a concentration of about 0.02 to 5.0 percent by weight of said N-vinyl lactam monomer, and said antimicrobial being present in a concentration sufficient to provide the resultant medical sealant composition with about 0.01 to 10 percent by weight antimicrobial;
   (b) exposing said composition to sufficient energy to result in the formation of a crosslinked swellable polymeric matrix;
   (c) grinding said polymer into a powder having an average particle size of less than about 0.25 cm;
   (d) adding said powder to a plasticizer solution, said plasticizing solution being present in a concentration of between about 55 and less than about 95 percent by weight of said medical sealant composition, and said powder and plasticizing solution being present in a concentration sufficient to provide said medical sealant composition with a T-Peel value of at least about 3 g/cm when measured on low density polyethylene, as described herein.

13. A caulkable medical sealant prepared according to the method of claim 11 wherein the amount of said N-vinyl lactam monomer is about 5-45 percent by weight of said sealant composition.

14. A caulkable medical sealant prepared according to the method of claim 12 wherein the amount of said N-vinyl lactam monomer is about 5-45 percent by weight of said sealant composition.

15. A wound or burn dressing laminate comprising a layer of the composition of claim 1 and a layer of a moisture vapor permeable backing sheet suitable for use in a surgical dressing.

16. The wound or burn dressing of claim 15, wherein said N-vinyl lactam monomer is present in a concentration of about 5-45 percent by weight of said sealant composition.

17. A medical sealant composition in accordance with claim 1 wherein at least 90 percent by weight of the monomeric component is comprised of one or more N-vinyl lactams.

18. A medical sealant composition in accordance with claim 1 wherein 100 percent by weight of the monomeric component is comprised of one or more N-vinyl lactams.

* * * * *

UNITED STATES PATENT AND TRADEMARK OFFICE
CERTIFICATE OF CORRECTION

PATENT NO. : 4,931,282

DATED : June 5, 1990

INVENTOR(S) : Robert A. Asmus and Daniel C. Duan

It is certified that error appears in the above-identified patent and that said Letters Patent is hereby corrected as shown below:

In Column 1, line 14, the formula "3,3'-ethylidene bis(N-vinyl-2-pYrrolidone) should read --3,3'-ethylidene bis(N-vinyl-2-pyrrolidone)--.
In Column 3, line 58, "antimicrobial" should read --antimicrobial;--.
In Column 10, line 43, "75" should read --275--.
In Columns 11 and 12, in Table I, Example 41, under the column % Solids (by wt.) "10" should read --100--.
In Column 15, line 10, "3 72" should read --3.72-- and "1 25" should read --1.25--.

Signed and Sealed this

Sixth Day of August, 1991

*Attest:*

HARRY F. MANBECK, JR.

*Attesting Officer*     *Commissioner of Patents and Trademarks*